United States Patent
Shirasawa et al.

[11] Patent Number: 6,154,283
[45] Date of Patent: Nov. 28, 2000

[54] METHOD FOR EVALUATING QUALITY OF LIQUID REPELLENT FILM

[75] Inventors: Atsushi Shirasawa, Susono; Masatsugu Nakanishi, Numazu, both of Japan

[73] Assignee: Toyota Jidosha Kabushiki Kaisha, Toyota, Japan

[21] Appl. No.: 09/146,520

[22] Filed: Sep. 3, 1998

[30] Foreign Application Priority Data

Nov. 17, 1997 [JP] Japan ................................ 9-315168

[51] Int. Cl.⁷ ............................ G01N 21/00; G01B 11/06
[52] U.S. Cl. ........................................... 356/432; 356/382
[58] Field of Search .................................. 356/445, 432, 356/436, 382

[56] References Cited

U.S. PATENT DOCUMENTS 4,591,271  5/1986  Byers ..................................... 356/445
5,144,151  9/1992  Thorne et al. ......................... 356/445

FOREIGN PATENT DOCUMENTS 60-21976    2/1985   Japan .
61-92767    5/1986   Japan .
63-158164   7/1988   Japan .
3-290380   12/1991   Japan .
4-338137   11/1992   Japan .

*Primary Examiner*—Frank G. Font
*Assistant Examiner*—Amanda Merlino
*Attorney, Agent, or Firm*—Oliff & Berridge, PLC

[57] ABSTRACT

The present invention relates to a method for evaluating a liquid repellent film on parts subjected to liquid repellent treatment, particularly to a method for evaluating the quality of a liquid repellent film comprising a substance absorbing or emitting electromagnetic waves, wherein the transmittance or reflectance ratio of electromagnetic waves, or fluorescence intensity is measured, and the characteristics of the liquid repellent film is evaluated from the graph of the relationship between a film thickness and a contact angle with a liquid having been determined in advance.

9 Claims, 2 Drawing Sheets

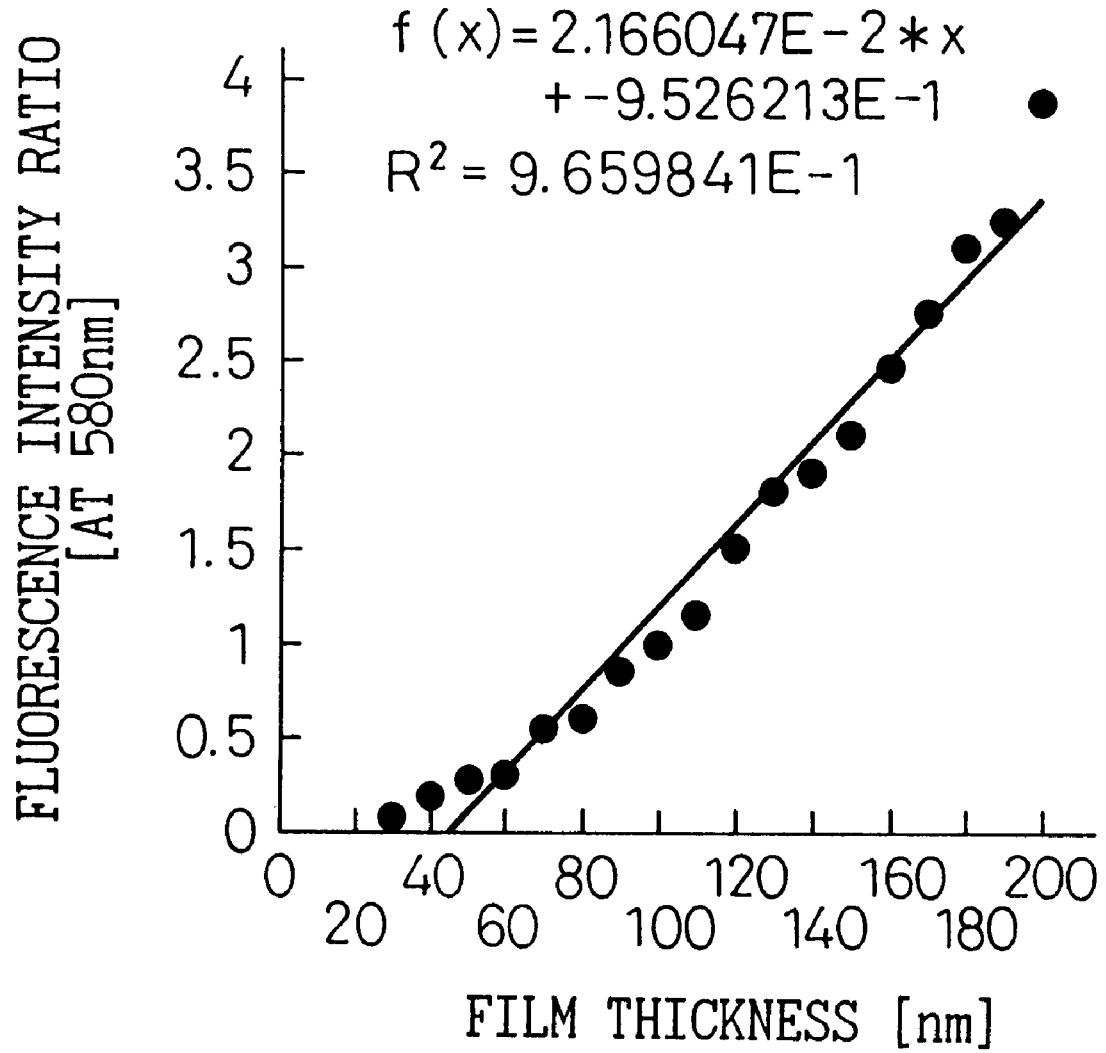

METHOD FOR EVALUATING QUALITY OF LIQUID REPELLENT FILM

BACKGROUND OF THE INVENTION

1. Field of the Invention

The present invention relates to a method for evaluating a liquid repellent film on parts which are subjected to a liquid repellent treatment. The present invention particularly relates to a method for evaluating the quality of a liquid repellent film wherein by containing a substance absorbing or emitting electromagnetic waves, the transmittance or reflectance ratio of electromagnetic waves, or fluorescence intensity is measured in a repellent film, and the characteristics of the liquid repellent film are evaluated from a map of the relationship between the film thickness and the contact angle with a liquid, which has been determined in advance.

2. Description of the Prior Art

A fuel injection valve (referred to as an injector hereinafter) of an internal combustion engine, etc. must surely stop a fuel flow or allow a suitable amount of the fuel to flow by opening or closing the valve. Moreover, foreign materials such as oil, additives and moisture are present in the fuel, and accumulations, which are so-called deposits and which hinder the flow of the fuel, etc., form while the engine is running. When deposits are accumulated, they hinder the fuel flow, and cause a failure of the internal combustion engine even if the injector constituent parts are prepared with high precision. Various parts have recently been improved by being subjected to a repellent film treatment for the purpose of decreasing the adhesion of such deposits. However, such a film is colorless and transparent in the visible light region, and very thin. As a result, discrimination of the film itself is difficult. When the film is not formed in a predetermined manner, the desired effects cannot be exhibited. Judgement of the formation of the liquid repellent film and evaluation of the film, therefore, becomes important.

The thickness of a film used for electronic and mechanical parts has heretofore been from around 100 nm to 0.1 mm. Observation of a cross section with an electron microscope, a fluorescent X-ray thickness meter, or the like used in the measurements cannot be used for measuring the thickness of a liquid repellent film having a thickness of up to 100 nm. In order to improve such measurement methods, the following methods have been proposed: a method for estimating the liquid repellency of a liquid repellent film from its optical properties; a method for estimating the liquid repellency from the physical properties of a liquid used in the inspection; and a method for estimating the liquid repellency wherein a liquid is used in the inspection, the liquid repellency and a capillary phenomenon act on the liquid, and the liquid repellency is estimated from the physical properties.

Although all the methods mentioned above are nondestructive ones, costly apparatuses such as an infrared spectrometer, a refractometer and a polarized light analyzer become necessary for measuring the optical properties. Moreover, attention and labor are required for handling and controlling the liquid in the method of using a liquid, and there is much restriction on the physical properties (including the shape, etc.) of the material to be measured.

On the other hand, Japanese Unexamined Patent Publication (Kokai) No. 4-338137 discloses a water repellent film obtained by substituting a fluoroalkyl group for part of a ceramic integrally formed on a glass substrate as a water repellent glass and mainly containing $SiO_2$.

Such a water repellent film is favorable to adhesion and hardness, and the treated film can be evaluated by the method as mentioned above. However, there still remain the same problems. Accordingly, development of an evaluation method is desired, which achieves the evaluation of such water repellent films, which solves the problems as mentioned above and which is simple and favorable in cost.

SUMMARY OF THE INVENTION

An object of the present invention is to investigate a method for evaluating the liquid repellency of a liquid repellent film for which a FAS film (glass or gel film containing a fluoroalkyl group) is used, and provide a method for evaluating the quality of a liquid repellent film which method can evaluate the liquid repellent film by adding a visible light-absorbing substance, and measuring the transmittance ratio of visible light.

Furthermore, another object of the present invention is to investigate a method for evaluating the liquid repellency of a liquid repellent film for which a FAS film (glass or gel film containing a fluoroalkyl group) is used, and provide a method for evaluating the quality of a liquid repellent film which method can evaluate the liquid repellent film by adding a coloring matter having a high solubility in a solvent and showing fluorescent properties, and irradiating the film with ultraviolet rays to emit fluorescence.

Furthermore, another object of the present invention is to investigate means capable of evaluating the initial characteristics of a liquid repellent film and the durability of the characteristics, and provide a method for evaluating the quality of a liquid repellent film which method is capable of evaluating the initial state of the liquid repellency and the durability from the density of fluorescent points per unit area.

Furthermore, another object of the present invention is to provide a method for evaluating the quality of a liquid repellent film which method is excellent in nondestructiveness, rapidly, reproducibility and quantitativeness as an evaluation means as explained above, which requires no skill for the measurement itself, and which can measure an area having a dimension at least less than a millimeter.

The gist of the present invention will be described as follows.

(1) A method for nondestructively evaluating the quality of a liquid repellent film formed on parts, comprising the steps of:

coating parts with a liquid repellent material containing a substance which absorbs electromagnetic waves having a specific wavelength, measuring the transmittance ratio of the electromagnetic waves having a specific wavelength in the coated portion of the parts, and evaluating the quality of the liquid repellent film from the transmittance ratio thereof.

(2) A method for nondestructively evaluating the quality of a liquid repellent film formed on parts, comprising the steps of:

coating parts with a liquid repellent material containing a substance which emits electromagnetic waves having a specific wavelength, measuring the intensity of the electromagnetic waves having a specific wavelength in the coated portion of the parts, and evaluating the quality of the liquid repellent film from the intensity thereof.

(3) The method for evaluating the quality of a liquid repellent film according to item (1), wherein the transmittance ratio of visible light is measured by transmitting visible light.

(4) The method for evaluating the quality of a liquid repellent film according to item (2), wherein the fluorescence intensity is measured by irradiating the film with ultraviolet rays to emit fluorescence.

(5) The method for evaluating the quality of a liquid repellent film according to item (2), wherein the substance is fluorescent dye such as heterocyclic coumarin, oxazine or naphthalic acid imide, or a fluorescent pigment obtained by coloring a resin powder with any of the fluorescent dyes.

(6) The method for evaluating the quality of a liquid repellent film according to item (1) or (2), wherein a substrate comprising silicic material, borosilicates or phosphate glass, or various resins such as fluororesins and silicone resins is used for forming the film.

BRIEF DESCRIPTION OF THE DRAWING

FIG. 3 is a graph showing the relationship between a film thickness and an intensity ratio of fluorescence in the present invention.

DETAILED DESCRIPTION OF THE PREFERRED EMBODIMENT

Figure 1:
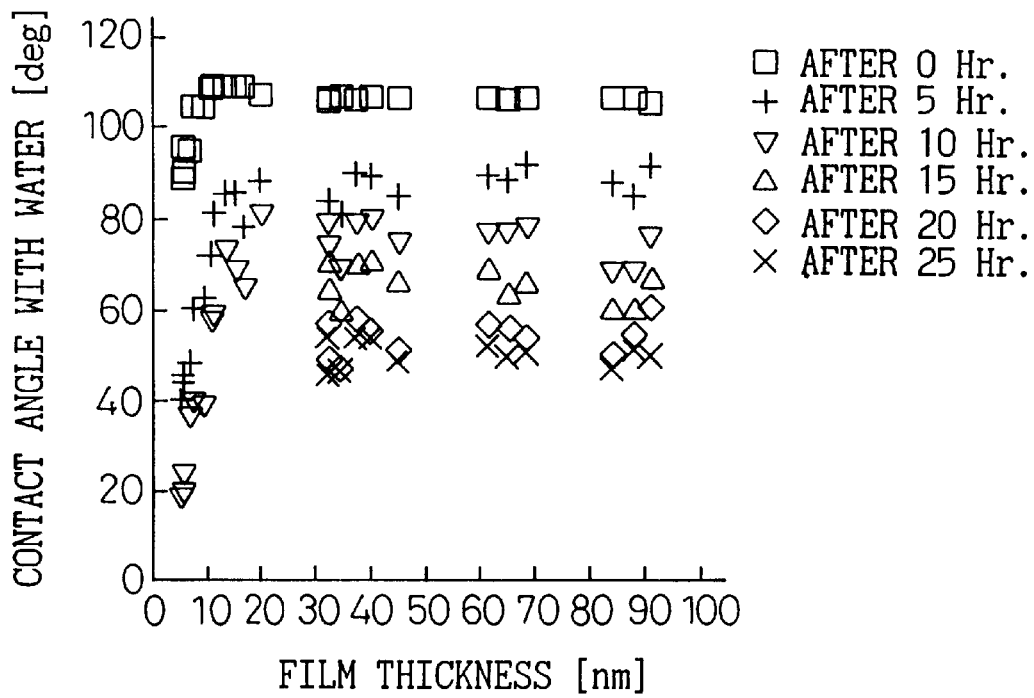
FIG. 1 is a graph showing the relationship between a film thickness and a contact angle with a liquid before and after a heat run test of the present invention.

Parts are coated with a film in which a substance absorbing electromagnetic waves is present as an admixture in the first aspect of the present invention; therefore, when the parts are irradiated with specific electromagnetic waves, the quality of the liquid repellent film can be evaluated from the difference of the transmittance ratio thereof. Parts are coated with a film in which a substance emitting electromagnetic waves is present as a mixture in the second aspect of the present invention; therefore, when the parts are irradiated with specific electromagnetic waves, the quality of the liquid repellent film can be evaluated from the intensity of the emitting waves.

More concretely, fluoroalkylsilane and tetraethoxysilane are used as starting materials, and a glass film containing a fluoroalkyl group which has liquid repellency (FAS film) is formed. A liquid repellent film in which a fluorescent coloring matter is uniformly dispersed can be obtained by adding, during the preparation of the FAS coating liquid, a coloring matter highly soluble in the solvent and showing fluorescence. When the liquid repellent film is irradiated with ultraviolet rays, the coloring matter emits fluorescent light. The existence of the liquid repellent film can be easily judged in a noncontact manner and nondestructively.

In the first aspect of the present invention, the film comprises all or any of the following substances: a metal alkoxide represented by the formula $M(OR)_n$ wherein M is a metal element, R is an alkyl group, and n is an oxidation number of the metal element, a substituted metal alkoxide obtained by substituting a fluoroalkyl group for part of alkoxyl groups, an organic polymer, water, an organic solvent, an acid and a base, and is prepared by a sol-gel method. A substance absorbing electromagnetic waves having a specific wavelength is introduced into the film in a given proportion per unit volume. On the other hand, there are high correlations among factors of the film as explained below: a film thickness and an initial liquid repellency as measured by the contact angle of the liquid; a film thickness and durability of the liquid repellent film evaluated from a change in the contact angle of the liquid caused by a heat run test; and a film thickness and a transmittance ratio of electromagnetic waves having a specific wavelength. The relationships can be individually obtained in advance. The presence of the film, the film thickness, the initial state of the liquid repellency and the durability of the film can be evaluated from the transmittance ratio, of light having a specific wavelength, of the film.

Examples of the metal element include Group I to Group V elements (A group and B group being included), Group VIB elements and lanthanide. The alkyl group includes isomeric structures. The oxidation number (n) of the metal elements is usually from 2 to 6.

Examples of the substance which transmits electromagnetic waves are typically glass used as a substrate, and the examples include silicic material, borosilicates and phosphate glass, or various resins such as fluororesins and silicone resins.

In the second aspect of the present invention, the film comprises all or any of the following substances: a metal alkoxide represented by the formula $M(OR)_n$ wherein M is a metal element, R is an alkyl group, and n is an oxidation number of the metal element, a substituted metal alkoxide obtained by substituting a fluoroalkyl group for an alkoxyl group, an organic polymer, water, an organic solvent, an acid and a base, and is prepared by a sol-gel method. A substance emitting electromagnetic waves is introduced into the film in a given proportion per unit volume. On the other hand, there are high correlations among factors of the film as explained below: a film thickness and an initial liquid repellency as measured by the contact angle of the liquid; a film thickness and durability of the liquid repellent film evaluated from a change in the contact angle of the liquid after a heat run test; and a film thickness and an intensity of electromagnetic waves having a specific wavelength. The relationships can be individually obtained in advance. The presence of the film, the film thickness, the initial state of the liquid repellency and the durability of the film can be evaluated from the intensity of electromagnetic waves having a specific wavelength of the film.

Examples of the substance emitting electromagnetic waves are fluorescent dyes such as heterocyclic coumarin as a fluorescent substance, oxazine and naphthalic acid imide, or fluorescent pigments obtained by coloring a resin powder with any of the fluorescent dyes as mentioned above.

The present invention will be explained below in more detail with reference to the examples.

EXAMPLES

Example 1

As an example of the first aspect in the present invention, $Si(OC_2H_5)_4$ and $CF_3(CF_2)_7CH_2CH_2Si(OM)_3$ were used as a metal alkoxide and a substituted metal alkoxide, respectively, and ethanol was used as a solvent. Moreover, aqueous hydrochloric acid was used as an acid and water. Rhodamine 6G was further added as a coloring matter in an amount of about $\frac{1}{1,000}$ in terms of a weight ratio, and a film having liquid repellency was formed on a 1 mm thick fused quartz plate containing 99.99% $SiO_2$.

An apparatus in Example 1 includes a simple device, for measuring transmittance ratio, which includes an optical path for incident light and transmitted light through a sample to be measured, a calculator for controlling the device for measuring transmittance ratio during the measurement, and for calculating the transmittance ratio (and film thickness) of the sample from the results thus measured, and a fixing jig and a stage for positioning and fixing the sample.

Figure 2:
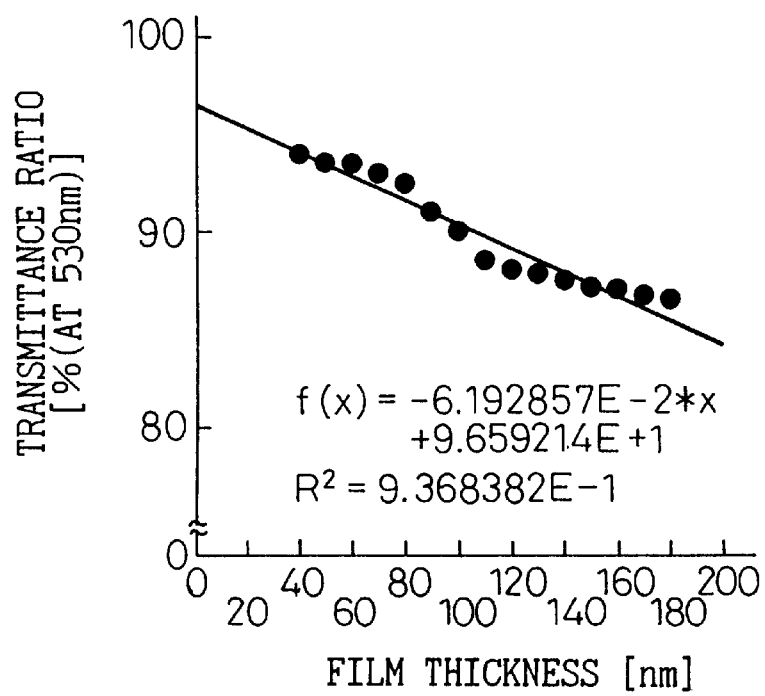
FIG. 2 is a graph showing the relationship between a film thickness and a light transmittance ratio in the present invention.

Measurements were made on the films using the apparatus mentioned above. FIG. 1 shows the relationship between a film thickness and an initial liquid repellency represented by a contact angle with water, and the relationship between a film thickness and a heat resistance of the liquid repellency represented by the change in contact angle with water after heat run tests in a high temperature bath at 400° C. with the heating time varied. Furthermore, FIG. 2 shows the relationship between a film thickness and a transmittance ratio of visible light having a wavelength of 530 nm.

The transmittance ratio of the liquid repellent film increases with a decrease in the film thickness, and becomes close to the light transmittance ratio of the substrate. The initial value (as a test for 0 hour) of the contact angle with a liquid and the extent of the variation in the contact angle after heat run tests are each approximately the same in a region where the film thickness is at least a specific value (10 nm in FIG. 1). When the film thickness is in a region of up to 10 nm, the initial value of the contact angle with the liquid and the value thereof subsequent to the heat run test decrease with a decrease in the film thickness. That is, although the variation of a liquid repellent film is the same when the film thickness is at least 10 nm, the film shows a poor initial property and rapid deterioration after the heat run test when the film thickness is less than 10 nm, for the reasons described below. In the course of deterioration of the liquid repellent film on a substrate, the functional groups are eliminated to form island-like intervals. However, a film having a thickness of at least 10 nm shows the same constant deterioration characteristics, and can be satisfactorily used as an evaluation index.

The measured range of the transmittance ratio is from about 0.1 to 1 mm in diameter. The light transmittance ratio is obtained by calculation from the intensity of the direct incident light in the range and that of the transmitted light. When the liquid repellent film is island-like, the intensity of the transmitted light is detected as a combined intensity of the transmitted light from the portion where the liquid repellent film exists and from the directly transmitted light from the substrate.

In a region where the liquid repellent film has a thickness of up to a value such that the visible light transmittance ratio varies, the liquid repellent film is island-like, and the phenomenon of apparent film thickness signifies that the area of portions where the liquid repellent film exists is decreased. The decrease also signifies that the fluoroalkyl groups having liquid repellency on the liquid repellent film surface are also decreased. Accordingly, the liquid repellency of the film is lowered with a decrease in the apparent film thickness. Moreover, in a region where the liquid repellent film has a thickness of at least the above-mentioned value, the liquid repellent film is uniform and membrane-like, and the density of the fluoroalkyl groups having liquid repellency is approximately constant on the liquid repellent film surface regardless of the apparent film thickness.

Furthermore, the deterioration of the liquid repellent film at high temperatures does not depend on an apparent film thickness obtained by the light transmission method, and is caused by breaking a specific bond of the fluoroalkyl group having liquid repellency, eliminating the fluoroalkyl group and decreasing the density of the fluoroalkyl group having liquid repellency on the liquid repellent film surface.

The sample having a liquid repellent film formed on the substrate substantially shows no change of the film thickness and the light transmittance ratio determined with a light transmission method before and after the heat run test at high temperatures. Moreover, the variation of the contact angle of the film with a liquid before and after the heat run test at high temperatures does not depend on the film thickness, and the contact angle varies with the same ratio.

It can be concluded from what has been explained above that the quality of the liquid repellent film (uniformity of the film, initial liquid repellency, durability of the liquid repellency at high temperatures) on a substrate can be evaluated from the light transmittance ratio obtained by a light transmission method. Moreover, in view of the principle of the light transmission method, the procedures as mentioned above can be applied when conditions as described below are satisfied.

The conditions of the substrate are as follows: (1) the substrate can transmit light (from the far infrared to the far ultraviolet regions); (2) the substrate has uniform optical properties on the surface as well as in the interior; (3) the substrate has a smooth surface such that light is not scattered; (4) the substrate has a sufficient curvature in the measurement range when the substrate has a curved surface with a secondary or a tertiary order; and (5) the substrate ensures the measurement range. The conditions of the liquid repellent film are as follows: (1) the film can transmit light (from the far infrared to the far ultraviolet regions); (2) the film has uniform optical properties within the film as well as at the interface thereof; (3) the film does not scatter light within the film and at the interface thereof; (4) the film has a sufficient curvature in the measurement range when the film has a curved surface with a secondary or a tertiary order; (5) the film ensures the measurement range; and (6) the film shows a correlation between the quality of the film and the light transmittance ratio obtained by the light transmission method. The other conditions are as follows: the positional relationship among optical analyzers on the light source side and the light receiving side can be fixed.

Example 2

As an example of the second aspect of the present invention, $Si(OC_2H_5)_4$ and $CF_3(CF_2)_7CH_2CH_2Si(OM)_3$ were used as a metal alkoxide and a substituted metal alkoxide, respectively. Ethanol was used as a solvent, and aqueous hydrochloric acid was used as an acid and water. Rhodamine 6G was further added as a coloring matter in an amount of about 1/1,000 in terms of a weight ratio, and a film having liquid repellency was formed on a 1 mm thick fused quartz plate containing 99.99% of $SiO_2$.

The apparatus in Example 2 includes a simple device for measuring transmittance ratio which includes an optical path for light incident on the sample to be measured and for the fluorescent light, a calculator for controlling the device for measuring the fluorescence intensity during the measurement, and calculating the fluorescence intensity (and film thickness) of the sample from the results thus measured, and a fixing jig and a stage for positioning and fixing the sample.

Measurements were made on the films using the apparatus mentioned above. FIG. 1 shows, in the same manner as in Example 1, the relationship between a film thickness and an initial liquid repellency represented by a contact angle with water, and the relationship between a film thickness and a heat resistance of the liquid repellency represented by the change in contact angle with water after heat run tests. FIG. 3 shows the relationship between a thickness of a film which is being irradiated with a visible light having a wavelength of 525 nm and a fluorescence intensity having a wavelength of 580 nm. In addition, the evaluation was made while the fluorescence intensity was defined to be 1 when the film thickness was 100 nm.

The fluorescence intensity of the liquid repellent film decreases as the film thickness decreases, and becomes close to the fluorescence intensity of the substrate. The initial value (as a test for 0 hour) of the contact angle with a liquid and the extent of variation in the contact angle after the heat run tests are each approximately the same in a region where the film thickness is at least a specific value (10 nm in FIG. 1). When the film thickness is in a region of up to 10 nm, the initial value of the contact angle with the liquid and the contact angle subsequent to the heat run tests decrease with a decrease in the film thickness. That is, although the variation of a liquid repellent film is the same when the film thickness is at least 10 nm, the film shows a poor initial property and rapid deterioration after the heat run tests when the film thickness is less than 10 nm for reasons as described below. In the course of deterioration of the liquid repellent film on a substrate, the functional groups are eliminated at island-like intervals. However, a film having a thickness of at least 10 nm shows the same constant deterioration characteristics, and can be satisfactorily used as an evaluation index.

It is understood from the relationships in FIGS. 1 and 3 that the thickness of the liquid repellent film, the initial characteristics of the liquid repellency of the film and the durability of the film at high temperatures can be estimated from the fluorescence intensity.

Since the methods of the present invention do not use a liquid, they are not influenced by the storage conditions and environmental conditions. Moreover, the methods are less restricted by the physical properties of materials to be measured, and the characteristics of the liquid repellent film on parts can be relatively simply measured. Accordingly, the accuracy and efficiency of inspection for the quality control of the liquid repellent film on injectors or the like can be improved.

What is claimed is:

1. A method for nondestructively evaluating the quality of a liquid repellent film formed on parts, comprising the steps of:

coating parts with a liquid repellent material containing a substance which absorbs electromagnetic waves having a specific wavelength, measuring the transmittance ratio of the electromagnetic waves having a specific wavelength in the coated portion of the parts, determining a film thickness from the transmittance ratio, and evaluating one of an initial state of liquid repellency and durability of the liquid repellent film from the film thickness thereof.

2. A method for nondestructively evaluating the quality of a liquid repellent film formed on parts, comprising the steps of:

coating parts with a liquid repellent material containing a substance which emits electromagnetic waves having a specific wavelength, measuring the intensity of the electromagnetic waves having a specific wavelength in the coated portion of the parts, determining a film thickness from the intensity, and evaluating one of an initial state of liquid repellency and durability of the liquid repellent film from the film thickness thereof.

3. The method for evaluating the quality of a liquid repellent film according to claim 1, wherein the transmittance ratio of visible light is measured by transmitting visible light.

4. The method for evaluating the quality of a liquid repellent film according to claim 2, wherein the fluorescence intensity is measured by irradiating the film with ultraviolet rays to emit fluorescence.

5. The method for evaluating the quality of a liquid repellent film according to claim 2, wherein the substance is a fluorescent dye such as heterocyclic coumarin, oxazine or naphthalic acid imide, or a fluorescent pigment obtained by coloring a resin powder with any of the fluorescent dyes.

6. The method for evaluating the quality of a liquid repellent film according to claim 1, wherein a substrate, comprising silicic material, borosilicates or phosphate glass, or various resins, is used for forming the film.

7. The method for evaluating the quality of a liquid repellent film according to claim 2, wherein a substrate, comprising silicic material, borosilicates or phosphate glass, or various resins, is used for forming the film.

8. The method for evaluating the quality of a liquid repellent film according to claim 6, wherein a resin selected from the group consisting of fluororesins and silicone resins is used for forming the film.

9. The method for evaluating the quality of a liquid repellent film according to claim 7, wherein a resin selected from the group consisting of fluororesins and silicone resins is used for forming the film.

* * * * *